United States Patent
Platzek et al.

(12)

(10) Patent No.: US 6,194,566 B1
(45) Date of Patent: Feb. 27, 2001

(54) PROCESS FOR THE PRODUCTION OF METALLOPORPHYRIN-METAL COMPLEX CONJUGATES

(75) Inventors: Johannes Platzek; Ulrich Niedballa, both of Berlin (DE)

(73) Assignee: Schering Aktiengesellschaft, Berlin (DE)

( * ) Notice: Subject to any disclaimer, the term of this patent is extended or adjusted under 35 U.S.C. 154(b) by 0 days.

(21) Appl. No.: 09/400,993

(22) Filed: Sep. 21, 1999

Related U.S. Application Data

(60) Provisional application No. 60/067,366, filed on Dec. 2, 1997.

(30) Foreign Application Priority Data

Sep. 22, 1998 (DE) .............................................. 198 45 782

(51) Int. Cl.[7] .......................... A61K 51/00; A61K 31/40; A61K 31/555; C07D 487/22; G01N 24/08
(52) U.S. Cl. ........................ 540/145; 424/1.65; 424/1.85; 424/9.61; 534/14; 534/15
(58) Field of Search .................................. 424/1.65, 1.85, 424/9.61; 540/145; 534/14, 15

(56) References Cited

U.S. PATENT DOCUMENTS

| 5,275,801 | * | 1/1994 | Niedballa et al. | 424/1.65 |
| 5,284,647 | | 2/1994 | Niedballa et al. | 424/81 |
| 5,849,259 | | 12/1998 | Hilger et al. | 424/1.65 |

FOREIGN PATENT DOCUMENTS

| 4 232 925 | 3/1994 | (DE) . |
| 0 336 879 | 10/1989 | (EP) . |
| 0 355 041 | 2/1990 | (EP) . |

OTHER PUBLICATIONS

Review Article., Mashiko and Dolphin., 21.1 Porphyrins . . . Corrins and Related Macrocycles. Porpyrins vol. 1–7, p. 82, Sep. 1978.*

* cited by examiner

*Primary Examiner*—Mukund J. Shah
*Assistant Examiner*—Pavanaram K Sripada
(74) *Attorney, Agent, or Firm*—Millen, White, Zelano & Branigan, P.C.

(57) ABSTRACT

Metalloporphyrin-metal complex conjugates are prepared by reacting a porphyrin-metal complex conjugate with a metal acetylacetoane in a solvent or solvent mixture at a temperature from room temperature to 150° C. in concentrations of 3–30% in the metalloporphyrin-metal complex conjugate.

28 Claims, No Drawings

PROCESS FOR THE PRODUCTION OF METALLOPORPHYRIN-METAL COMPLEX CONJUGATES

This application claims the benefit of the filing date of U.S. Provisional Application Serial No. 60/067,366, filed Dec. 2, 1997.

The invention relates to the subject that is characterized in the claims, i.e., a process for the production of metalloporphyrin-metal complex conjugates that contain at least one ion of an element of atomic numbers 20–32, 37–39, 42–51 or 57–83 in the complex part of the conjugate. Up until now, metalloporphyrin-metal complex conjugates were produced according to multistage processes. In EP 0 336 879, tetraphenylporphyrins are first reacted with a complexing agent, then with a metal oxide or metal salt for complexing the complexing agent and then with manganese acetate for substitution of the pyrrolic NH groups. The reaction with manganese acetate is carried out at 80° C. in glacial acetic acid. The use of the acetate has the drawback that it is not possible to work either with excesses or under anhydrous conditions. The usability of this process is therefore limited.

From EP 0 355 041 is known a process for the production of metalloporphyrin-metal complex conjugates, in which first the manganese is inserted into the porphyrin core, and then the reaction is carried out with a complexing agent and a metal oxide or metal salt for complexing the complexing agent. This procedure has a decisive drawback. The immobilization on the metal in the porphyrin is carried out as early as in the first stage, so that for a variation of the porphyrin metal in the case of uniform complexing agents, the synthesis for each new porphyrin metal must be performed each time for at least three stages. In this case, it is not possible to avoid drawbacks such as, e.g., losses in yield and effects in the area of environmental protection, such as, e.g., an increase in the amount of metal-containing wastes.

The object of this invention was therefore to provide a synthesis method for metalloporphyrin-metal complex conjugates, which does not exhibit the above-mentioned drawbacks, but mainly makes possible a more economical synthesis scheme in the case of variation of the porphyrin metal and the presence of sensitive groups.

This object is achieved by the process according to the invention, as it is characterized in the claims.

This is a process for the production of metalloporphyrin-metal complex conjugates, which is characterized in that a porphyrin-metal complex conjugate is converted into a metalloporphyrin-metal complex conjugate by reaction with a metal acetylacetonate in a protic or aprotic polar solvent or solvent mixture at temperatures from room temperature to 150° C. at concentrations of 3–30%.

The insertion of the central metal atom into the porphyrin core is carried out by a recomplexing reaction with metal acetylacetonate, i.e., the metal that is already bonded in a complex manner in the acetylacetonate makes a switch from its complex ligand acetylacetone to complex ligand porphyrin and is also bonded in a complex manner by the latter.

A special embodiment of the invention is a process for the production of metalloporphyrin-metal complex conjugates of general formula I

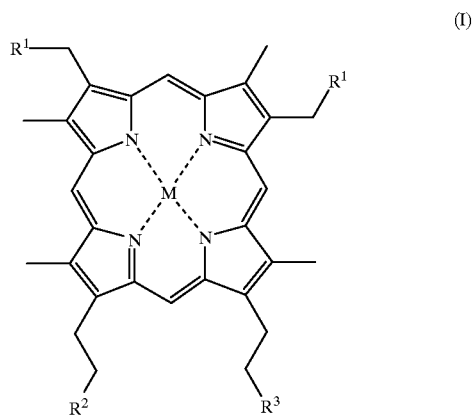

that contain at least one ion of an element of atomic numbers 20–32, 37–39, 42–51 or 57–83 in the complex part of the molecule, in which M stands for an ion of metals magnesium, aluminum, chromium, manganese, iron, cobalt, nickel, copper, zinc, gallium, technetium, indium, tin, europium, lutetium, thallium, bismuth or oxovanadium(IV), $R^1$ stands for a hydrogen atom, for a straight-chain $C_1$–$C_6$ alkyl radical, a $C_7$–$C_{12}$ aralkyl radical or for a group OR',
whereby R' is a hydrogen atom or a $C_1$–$C_3$ alkyl radical, $R^2$ stands for $R^3$, a group —CO—Z or a group —(NH)$_o$—(A)$_q$—NH—D,
whereby Z is a group —OL, with L in the meaning of an inorganic or organic cation or a $C_1$–$C_4$ alkyl radical,
A means a phenylenoxy group or a $C_1$–$C_{12}$ alkylene or $C_7$–$C_{12}$ aralkylene group that is interrupted by one or more oxygen atoms,
o and q, independently of one another, mean the numbers 0 or 1,
D means a hydrogen atom or a group —CO—A—(COOL)$_o$—(H)$_m$, with m equal to 0 or 1 and provided that the sum of m and o is equal to 1, $R^3$ stands for a group —(C=Q)(NR$^4$)$_o$—(A)$_q$—(NR$^5$)—K,
whereby Q stands for an oxygen atom or for two hydrogen atoms,
$R^4$ means an —(A)$_q$—H group, and
K means a complexing agent of general formula (IIa), (IIb), (IIc), (IId) or (IIe), and
$R^5$, if K is a complexing agent of Formula (IIa), has the same meaning as $R^4$, and if K is a complexing agent of Formula (IIb), (IIc), (IId) or (IIe),
$R^5$ has the same meaning as D, provided that a direct oxygen-nitrogen bond is not allowed
and K stands for a complexing agent of general formulas (IIa), (IIb), (IIc), (IId) or (IIe)

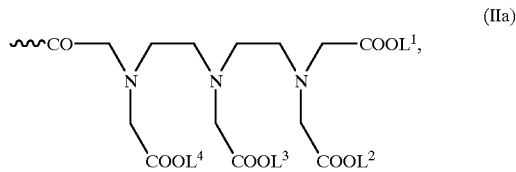

-continued

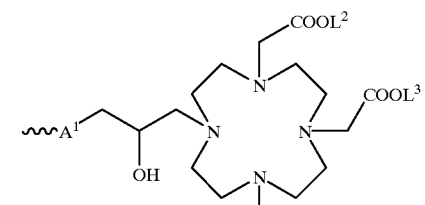
(IIb)

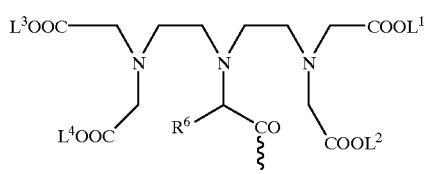
(IIc)

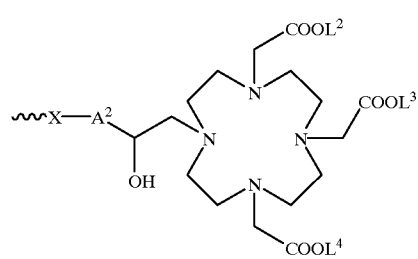
(IId)

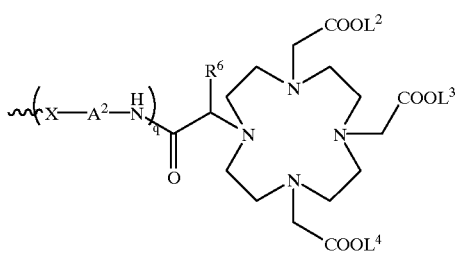
(IIe)

in which
o and q have the above-indicated meanings,
$A^1$ has the meaning that is indicated for A,
$R^6$ stands for a hydrogen atom, a straight-chain or branched $C_1$–$C_7$ alkyl group, a phenyl or benzyl group,
$A^2$ stands for a phenylene group, a —$CH_2$—NHCO—$CH_2$—CH($CH_2$COOH)—$C_6H_4$—β group, a phenylenoxy group or a $C_1$–$C_{12}$ alkylene or $C_7$–$C_{12}$ aralkylene group that is optionally interrupted by one or more oxygen atoms, 1 to 3 —NHCO and/or 1–3 CONH groups and/or substituted with 1 to 3 —$(CH_2)_{0-5}$COOH groups,
whereby β stands for the binding site to X,
X stands for a —CO— or NHCS group, and
$L^1$, $L^2$, $L^3$, and $L^4$, independently of one another, stand for a metal ion equivalent of an element of the above-mentioned atomic numbers, provided that at least two of these substituents stand for a metal ion equivalent, and other anions are present to compensate for optionally present charges in the metalloporphyrin-metal complex conjugate and in which free carboxylic acid groups that are not required for complexing can also be present as salts with physiologically compatible inorganic and/or organic cations or as esters or as amides,
characterized in that
porphyrin-metal complex conjugates of general formula (III)

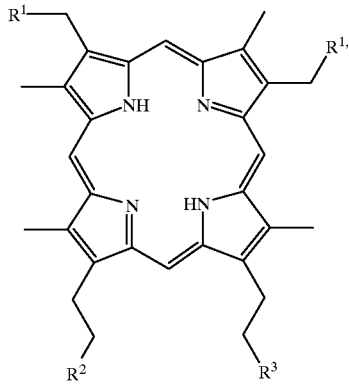
(III)

in which $R^1$, $R^2$, $R^3$ and $R^4$ have the above-indicated meanings, are converted into metalloporphyrin-metal complex conjugates of Formula (I) by reaction with a metal acetylacetonate of metal M in a protic or aprotic polar solvent or solvent mixture at temperatures from room temperature to 150° C. in concentrations of 3–30%.

As metal M, the metals magnesium, aluminum, chromium, manganese, iron, cobalt, nickel, copper, zinc, gallium, technetium, indium, tin, europium, lutetium, thallium, bismuth and oxovanadium(IV) are suitable. Preferred are magnesium, aluminum, chromium, manganese, iron, cobalt, nickel, copper, zinc, tin, lutetium and oxovanadium(IV). Especially preferred are manganese, iron, copper and zinc.

The metals are present in porphyrin, if not otherwise indicated, as divalent or trivalent ions. If an ion that is bonded in the porphyrin is present in a higher oxidation stage than +2, the excess charge(s) are compensated for by, e.g., anions of organic or inorganic acids, preferably by acetate, tartrate, succinate, maleate, chloride, sulfate and nitrate ions or by negative charges that are present in $R^2$ and/or $R^3$.

Preferred alkyl radicals $R^1$ are straight-chain $C_1$–$C_3$ alkyl radicals. Especially preferred is the methyl radical.

Alkyl radical R' can be a methyl, ethyl, propyl or isopropyl radical.

Aralkyl radicals $R^1$ can be benzyl or 4-methoxybenzyl.

Inorganic cations L are, for example, the lithium ion and the potassium ion, especially the sodium ion.

Organic cations L are, for example, cations of organic bases; cations of primary, secondary or tertiary amines, such as, for example, ethanolamine, diethanolamine, morpholine, glucamine, N,N-dimethylglucamine, especially meglumine, can be mentioned.

Alkyl radical Z can be straight-chain or branched. Methyl and ethyl are preferred.

$R^2$ and $R^3$ preferably stand for the same radical. $R^2$ and $R^3$ preferably stand for groups —CONHNH—K, —CONH—$(CH_2)_2$—NH—K, —CONH—$(CH_2)_3$—NH—K, —CONH—$(CH_2)_4$—NH—K and —CONH—$(CH_2)_2$—O—$(CH_2)_2$—NH—K. Especially preferred is the group —CONHNH—K.

The meaning of an oxygen atom is preferred for Q.

$R^4$ is preferably hydrogen.

Preferred complexing agents K are complexing agents of Formulas IIa and IIe.

$R^6$ preferably stands for a hydrogen atom or a methyl group.

$A^2$ preferably stands for a —CH$_2$—, —(CH$_2$)$_2$—, —CH$_2$OC$_6$H$_5$—β, —CH$_2$OCH$_2$—, —C$_6$H$_5$—, —CH$_2$—NHCO—CH$_2$—CH(CH$_2$COOH)—C$_6$H$_5$—β group, whereby β stands for the binding site to X.

X preferably stands for the CO group.

Especially preferred compounds are:

{μ-[{16,16'-{Zinc(II)-7,12-diethyl-3,8,13,17-tetramethylporphyrin-2,18-diyl]-bis[3,6,9-tris(carboxymethyl)-11,14-dioxo-3,6,9,12,13-pentaazahexadecanoato]}(8-)]}digadolinato(2-), disodium, {μ-[{16,16'-[Acetatomanganese(III)-7,12-diethyl-3,8,13,17-tetramethylporphyrin-2,18-diyl]-bis[3,6,9-tris(carboxymethyl)-11,14-dioxo-3,6,9,12,13-pentaazahexadecanoato]}-(8-)]}digadolinato(2-), disodium, {μ-[{16,16'-[Acetatoiron(III)-7,12-diethyl-3,8,13,17-tetramethylporphyrin-2,18-diyl]-bis[3,6,9-tris(carboxymethyl)-11,14-dioxo-3,6,9,12,13-pentaazahexadecanoato]}(8-)]}digadolinato(2-), disodium, and {μ-[{16,16'-[Copper(II)-7,12-diethyl-3,8,13,17-tetramethylporphyrin-2,18-diyl]-bis[3,6,9-tris(carboxymethyl)-11,14-dioxo-3,6,9,12,13-pentaazahexadecanoato]}(8-)]}-digadolinato(2-), disodium.

This process is especially advantageous compared to the prior art.

Metal acetylacetonates are solids that can easily be filtered off from the reaction mixture when working with excesses, but this is not the case with acetates.

Metal acetylacetonates can be dried very well in contrast to, e.g., acetates, which is necessary for a reaction scheme whereby water is excluded. Specifically for use in reactions on an industrial scale, good drying is of great advantage, since large amounts of adhering water adversely affect the course of the reaction.

When metal acetylacetonates are used, a simple separation of the first metal ligand is possible, and without ions if so desired, since acetylacetonate can also be recovered as acetylacetone and recycled in the reaction cycle. The expensive separation (e.g., of acetates) and disposal of accumulating salts or other solids, such as, e.g., salicylic acid with use of salicylates, are no longer necessary.

The recycling of acetylacetone in the reaction cycle makes possible an environmentally friendly reaction scheme.

Since excesses cause no problems, as mentioned above, the reaction kinetics can be influenced by use of metal acetylacetonate excesses, i.e., a shortening of the reaction times is possible by use of acetylacetonate excesses.

Because of the incorporation of the central metal atom in the last step, many porphyrins of the same skeleton can easily be synthesized with different central metal atoms, without the entire synthesis having to be repeated for each new central atom (more efficient reaction scheme).

An incorporation of different metals with positive charges in two or three places in the porphyrin core is possible without disruption by the respective metal complex ligands.

The incorporation of the central metal atom is carried out without metal exchange in the complexing agent part. Based on the high thermodynamic constants of DTPA-amides, it is astonishing and unexpected that a metal exchange does not result, which would lead to mixed complexes.

The product is obtained in high yields.

An especially high purity of the product is achieved.

The metals are used as acetylacetonates.

As solvents, protic or aprotic polar solvents, such as, e.g., acetic acid, formic acid, water, methanol, ethanol, dimethylformamide, formamide, dimethyl sulfoxide, pyridine or mixtures of two or more of the mentioned solvents are suitable. Preferred are glacial acetic acid, water and mixtures of the two solvents.

The reaction time is 1–24 hours, preferably 3–12 hours, especially preferably 3–8 hours.

The reaction temperature lies in a range of 20° C. to 150° C. The preferred range is 50° C. to 130° C., and the especially preferred range is 70° C. to 120° C.

In the case of typical isolation, the product is first precipitated (a) or the reaction mixture is concentrated by evaporation (b). In the case of precipitation, precipitating agents such as, e.g., acetone, diethyl ether, diisopropyl ether, or tetrahydrofuran are added, the suspension is filtered, and the crude product is dried.

The crude product that consists of (a) or (b) is dissolved in water, set at pH 7.2 and freeze-dried. Depending on purity, it is then chromatographed on silica gel or RP-18 and then freeze-dried after crystallization, dialyzed, or ultrafiltration (e.g., 1000 D membrane) is performed.

The examples below are used for a more detailed explanation of the subject of the invention, without intending that it be limited to these examples.

The starting porphyrins that are used for the syntheses of the metalloporphyrin-metal complex conjugates are described below:

SYNTHESIS INSTRUCTIONS 1

{μ[{16,16'-[7,12-Diethyl-3,8,13,17-tetramethyl-porphyrin-2,18-diyl]-bis [3,6,9-tris(carboxymethyl)-11,14-dioxo-3,6,9,12,13-pentaaza-hexadecanoato]}(8-)]}-digadolinato(2-), disodium Production is carried out according to Example 1c of WO 94/07894.

Yield: 1.19 g (70.1% of theory) of reddish-brown powder Elementary analysis (relative to anhydrous substance): Cld: C, 43.88; H, 4.51; Gd, 18.53; Na, 2.71; Fnd: C, 43.71; H, 4.30; Gd, 18.28; Na, 2.80.

SYNTHESIS INSTRUCTIONS 2a

{7,12-Diethyl-3,8,13,17-tetramethyl-2,18-bis[15,15-dimethyl-3,6,13-trioxo-8-(2-{N,N-bis[(tert.butoxycarbonyl)methyl]amino}-ethyl)-11-[(tert-butoxycarbonyl)-methyl]14-oxa-4,5,8,11-tetraazahexadec-1-yl}-porphyrin 8.31 g (13.45 mmol) of 3,9-bis(tert-butoxycarbonylmethyl)-6-carboxymethyl-3,6,9-triazaundecanedioic acid-di-tert-butyl ester, produced according to DE 19 50 78 19, Example 1f, and 2.09 g (15 mmol) of 4-nitrophenol are dissolved in 60 ml of dimethylformamide, and 5.16 g (25 mmol) of N,N-dicyclohexylcarbodiimide is added at 0° C. It is stirred for 3 hours at 0° C., then overnight at room temperature. 2 g (3.36 mmol) of 3,3'-(7,12-diethyl-3,8,13,17-tetramethylporphyrin-2,18-diyl)-di(propanohydrazide), produced according to H. Fischer, E. Haarer and F. Stadler, Z. Physiol. Chem., 241, 209 (1936), (dissolved in 50 ml of pyridine) is added in drops to the active ester solution that is thus produced, and it is stirred overnight. It is evaporated to the dry state in a vacuum, and the residue is chromatographed on silica gel (mobile solvent: dichloromethane/2-propanol=20:1).

Yield: 5.24 g (87% of theory) of a dark brown solid; Elementary analysis (relative to anhydrous substance): Cld: C, 62.92; H, 8.31;N, 10.93; Fnd: C, 62.81; H, 8.45; N, 10.80.

SYNTHESIS INSTRUCTIONS 2b)

{µ[{13,13'-[7,12-Diethyl-3,8,13,17-tetramethyl-porphyrin-2,18-diyl]-bis{3-carboxymethyl-6-(2-{N,N-bis[(carboxy)methyl]amino}ethyl)-8,11-dioxo-3,6,9,10-tetraazatridecanoato]}(8-)]}digadolinato (2-), disodium 5 g (2.79 mmol) of the title compound of synthesis instructions 2a is dissolved in 100 ml of trifluoroacetic acid and stirred for 8 hours at room temperature. It is evaporated to the dry state in a vacuum. The ligand that is thus obtained is dissolved in 100 ml of water, and 1.01 g (2.79 mmol) of gadolinium oxide is added. It is stirred at 60° C., and the pH is kept at 5 by adding 1N aqueous sodium hydroxide solution. The solution is filtered, and the filtrate is set at pH 7.2 with 1N aqueous sodium hydroxide solution. Then, it is chromatographed on RP 18 (mobile solvent: gradient that consists of water/acetonitrile).

Yield: 4.40 g (95% of theory) of an amorphous solid Water content: 10.3%. Elementary analysis (relative to anhydrous substance): Cld: C, 43.86; H, 4.51; N, 11.55; Gd, 18.52; Na, 2.71; Fnd: C, 43.61; H, 4.70; N, 11.38; Gd, 18.37; Na, 2.50.

SYNTHESIS INSTRUCTIONS 3

{10,10'-(µ-{10,10'-(7,12-Diethyl-3,8,13,17-tetramethylporphyrin-2,18-diyl)bis[(1RS)-1-methyl-2,5,8-trioxo-3,6,7-triaza-dec-1-yl]})bis[1,4,7,10-tetraazacyclododecane-1,4,7-triacetato(3-)]}digadolinium 8.47 g (13.45 mmol) of the Gd complex of 10-(4-carboxy-2-oxo-3-aza-1-methyl-butyl)-1,4,7,10-tetraazacyclododecane-1,4,7-triacetic acid, produced according to PCT/EP 97/06593, 0.64 g of lithium chloride (15 mmol) and 2.09 g (15 mmol) of 4-nitrophenol are dissolved in 100 ml of dimethyl sulfoxide at 50° C. After cooling to room temperature, 5.16 g (25 mmol) of N,N'-dicyclohexylcarbodiimide is added and preactivated for 12 hours. 2.0 g (3.36 mmol) of 3,3'-(7,12-diethyl-3,8,13,17-tetramethylporphyrin-2,18-diyl)di(propanohydrazide) and 0.71 g (7 mmol) of triethylamine are added to the solution that is thus produced, and it is stirred overnight at room temperature. The suspension that is obtained is then mixed with sufficient acetone until precipitation occurs, the precipitate is suctioned off, dried, taken up in water, insoluble dicyclohexylurea is filtered off, and the filtrate is chromatographed on RP 18 (mobile solvent: gradient that consists of tetrahydrofuran/water).

Yield: 5.07 g (83% of theory) of a dark brown amorphous powder; Water content: 7.9%. Elementary analysis (relative to anhydrous substance): Cld: C, 47.56; H, 5.43; N, 13.87; Gd, 17.30; Fnd: C, 47.42; H, 5.53; N, 13.68; Gd, 17.15.

SYNTHESIS INSTRUCTIONS 4

Conjugate that consists of 3,3'-(7,12-diethyl-3,8,13,17-tetramethylporphyrin-2-18-diyl)di(propanohydrazide) and 10-[7-(4-isothiocyanatophenyl)-2-hydroxy-5-oxo-7-(carboxymethyl)-4-aza-heptyl)]-1,4,7-tris (carboxylatomethyl)-1,4,7,10-tetraazacyclododecane, gadolinium complex, sodium salt ({10,10'-{µ-[(7,12-Diethyl-3,8,13,17-tetramethylporphyrin-2, 18-diyl)bis{(1-oxo-propane-3,1-diyl)hydrazino-thiocarbonylamino-4, 1-phenylene[(3RS)-3-carboxymethyl-1-oxopropane-3,1-diyl]amino (2-hydroxypropane-3,1-diyl)}]}bis[1,4,7,10-tetraazacyclododecane-1,4,7-triacetato(4-)]}digadolinium, disodium 1.01 g (10 mmol) of triethylamine is added to 594.8 mg (1 mmol) of 3,3'-(7,12-diethyl-3,8,13,17-tetramethylporphyrin-2,18-diyl)di(propanohydrazide) and 1806 mg (2.2 mmol) of 10-[7-(4-isothiocyanatophenyl)-2-hydroxy-5-oxo-7-(carboxymethyl)-4-aza-heptyl)-1,4,7-tris (carboxylatomethyl)-1,4,7,10-tetraazacyclododecane, Gd complex, sodium salt, produced according to WO 94/07894, Example 1, in 50 ml of water, and it is stirred for 12 hours at room temperature. It is evaporated to the dry state in a vacuum and chromatographed on silica gel (mobile solvent: methanol/water/glacial acetic acid=10/5/1). The product-containing fractions are evaporated to the dry state, the residue is dissolved in 100 ml of water and set at pH 7.2 with 2N sodium hydroxide solution. Then, it is freeze-dried.

Yield: 2.03 g (89% of theory) of a dark brown powder. Water content: 7.9%. Elementary analysis (relative to anhydrous substance): Cld: C, 48.45; H, 5.22; N, 12.28; S, 2.81; Gd, 13.79; Na, 2.02; Fnd: C, 48.37; H, 5.37; N, 12.15; S, 2.72; Gd, 13.58; Na, 1.75.

EXAMPLE 1

Instructions for the Production of Metalloporphyrin-Metal Complex Conjugates that Consist of the Porphyrin-Metal Complex Conjugates According to Synthesis Instructions 1 to 4 in the Example of a Porohyrin-Metal Complex Conjugate According to Synthesis Instructions 1

{µ[{16,16'-[Copper(II)-7,12-diethyl-3,8,13,17-tetramethylporphyrin-2,18-diyl]-bis[3,6,9-tris (carboxymethyl)-11,14-dioxo-3,6,9,12,13-pentaazahexadecaboato]}(8-)]}-digadolinato(2-), disodium 3 g (17.3 mmol) of the compound of synthesis instructions 1b) (porphyrin of type A) is added to 250 ml of acetic acid and mixed with 0.450 g (17.3 mmol, or optionally up to 30% excess) of copper(II)acetonylacetonate. It is heated for 3.5 hours to 119° C., whereby light is excluded and the procedure is performed under nitrogen.

Then, it is concentrated by evaporation in a vacuum, acetic acid residues are removed by codistillation with toluene, it is digested with ethyl acetate, and the solid is suctioned off. The solid is dissolved-in water and chromatographed on silica gel RP-18. It is eluted with a gradient that consists of water/methanol. The product-containing fractions are evaporated to the dry state in a vacuum. The residue is dissolved in water and set at a pH of 7.2 with 1N sodium hydroxide solution. It is filtered, and the product is obtained by freeze-drying.

Yield: 3.05 g (98% of theory); Elementary analysis (relative to anhydrous substance): Cld: C, 42.33; H, 4.24; N, 11.15; Cu, 3.61; Gd, 17.88; Na, 2.61; Fnd: C, 42.45; H, 4.31; N, 11.00; Cu, 3.70; Gd, 18.01; Na, 2.71.

The compounds that are cited in Tables 1–4 were synthesized according to these generally applicable production instructions.

Table 1: Incorporation of metal ions as central atoms into the Gd complex of porphyrins, which were produced according to Instructions 1.

Table 2: Incorporation of metal ions as central atoms into the Gd complex of porphyrins, which were produced according to Instructions 2.

Table 3: Incorporation of metal ions as central atoms into the Gd complex of porphyrins, which were produced according to Instructions 3.

Table 4: Incorporation of metal ions as central atoms into the Gd complex of porphyrins, which were produced according to Instructions 4.

EXAMPLE 2

{µ[16,16'-[Copper(II)-7,12-diethyl-3,8,13,17-tetramethylporphyrin-2,18-diyl]-bis[3,6,9-tris (carboxymethyl)-11,14-dioxo-3,6,9,12,13-pentaazahexadecaboato ]}(8-)]}-digadolinato(2-), disodium 25.0 kg (14.72 mol) of the compound of synthesis instructions 1b) is dissolved in 500 l of glacial acetic acid, mixed in portions with 3854.3 g (14.72 mol) of copper(II) acetylacetonate while being stirred, and heated with light excluded and a nitrogen cover gas for 6 hours to 120° C. Then, it is concentrated by evaporation in a vacuum. Acetic acid residues are largely removed by codistillation with toluene, the residue is digested with ethyl acetate, the solid is suctioned off and dried at 70° C. in a circulating air drier.

Yield: 25.12 kg (97% of theory). Elementary analysis (relative to anhydrous substance): Cld: C, 42.33; H, 4.24; N, 11.15; Cu, 3.61; Gd, 17.88; Na 2.61; Fnd: C, 42.46; H, 4.36; N, 11.01; Cu, 3.56; Gd, 17.79; Na 2.70.

TABLE 1

Incorporation of Metal Ions in the Gadolinium Complex of Prophyrins from Instructions 1

| Metall | Lösungsmittel | Zeit [h] | Temperatur [° C.] | Ausbeute [%] | Elementaranalyse [berechnet/gefunden] |
|---|---|---|---|---|---|
| $Fe^{3+}$ | HOAc/DMF 1:1 | 6 | 120 | 89 | C 41.67 H 4.17 N 10.97 Gd 17.60 Cl 1.98 Fe 3.13 Na 2.57<br>C 41.80 H 4.28 N 11.13 Gd 17.45 Cl 2.08 Fe 3.21 Na 2.69 |
| $Mn^{3+}$ | HOAc | 5 | 100 | 85 | C 41.69 H 4.18 N 10.98 Gd 17.61 Cl 1.98 Mn 3.08 Na 2.57<br>C 41.56 H 4.31 N 11.12 Gd 17.75 Cl 2.10 Mn 3.15 Na 2.65 |
| $Co^{3+}$ | HOAc/CHCl$_3$ 1:1 | 7 | 70 | 86 | C 41.59 H 4.17 N 10.95 Gd 17.57 Cl 1.98 Co 3.29 Na 2.57<br>C 41.47 H 4.26 N 11.09 Gd 17.68 Cl 2.05 Co 3.37 Na 2.66 |
| $Lu^{3+}$ | HOAc/DMF 1:1 | 6 | 100 | 87 | C 39.07 H 3.91 N 10.29 Gd 16.50 Cl 1.86 Lu 9.18 Na 2.41<br>C 39.02 H 4.11 N 10.15 Gd 16.38 Cl 1.87 Lu 9.27 Na 2.48 |
| $Al^{3+}$ | HOAc | 6 | 100 | 86 | C 42.35 H 4.24 N 11.15 Gd 17.89 Al 1.53 Cl 2.02 Na 2.62<br>C 42.47 H 4.36 N 11.04 Gd 17.78 Al 1.46 Cl 2.00 Na 2.53 |
| $Cr^{3+}$ | HOAc/CHCl$_3$ 1:1 | 8 | 70 | 90 | C 41.76 H 4.18 N 11.00 Gd 17.64 Cl 1.99 Cr 2.92 Na 2.58<br>C 41.85 H 4.27 N 11.20 Gd 17.77 Cl 2.12 Cr 3.01 Na 2.66 |
| $Ni^{2+}$ | HOAc/CHCl$_3$ 1:1 | 6 | 70 | 92 | C 42.44 H 4.25 N 11.18 Gd 17.93 Na 2.62 Ni 3.35<br>C 42.51 H 4.33 N 11.03 Gd 18.02 Na 2.70 Ni 3.41 |
| $Cu^{2+}$ | HOAc/H$_2$O 1:1 | 8 | 100 | 93 | C 42.32 H 4.24 N 11.15 Gd 17.88 Cu 3.61 Na 2.61<br>C 42.21 H 4.30 N 11.22 Gd 17.75 Cu 3.72 Na 2.70 |
| $Mg^{2+}$ | HOAc | 6 | 100 | 86 | C 43.20 H 4.34 N 11.40 Gd 18.28 Mg 1.41 Na 2.67<br>C 43.28 H 4.50 N 11.49 Gd 18.16 Mg 1.46 Na 2.43 |
| $Zn^{2+}$ | HCO$_2$H/CHCl$_3$ 1:1 | 6 | 70 | 82 | C 42.28 H 4.24 N 11.13 Gd 17.86 Na 2.61 Zn 3.71<br>C 42.38 H 4.33 N 11.18 Gd 17.98 Na 2.55 Zn 3.62 |
| $Sn^{2+}$ | HCO$_2$H | 6 | 100 | 81 | C 41.04 H 4.11 N 10.81 Gd 17.63 Na 2.53 Sn 6.54<br>C 41.15 H 4.20 N 10.93 Gd 17.74 Na 2.65 Sn 6.42 |
| $VO^{2+}$ | HOAc/DMF 1:1 | 7 | 100 | 84 | C 42.25 H 4.23 N 11.12 Gd 17.84 Na 2.61 V 2.89<br>C 42.14 H 4.30 N 11.00 Gd 17.91 Na 2.72 V 2.97 |

[Key to Table 1:]
Metall = Metal
Lösungsmittel = Solvent
Ziet [h] = Time [hours]
Temperatur [° C.] = Temperature [° C.]
Ausbeute [%] = Yield [%]
Elementaranalyse [berechnet/gefunden] = Elementary Analysis [theoretical/empirical]

TABLE 2

Incorporation of Metal Ions in the Gadolinium Complex of Porphyrins from Instructions 2

| Metall | Lösungsmittel | Zeit [h] | Temperatur [° C.] | Ausbeute [%] | Elementaranalyse [berechnet/gefunden] |
|---|---|---|---|---|---|
| $Fe^{3+}$ | HOAc | 6 | 120 | 87 | C 41.67 H 4.17 N 10.97 Gd 17.60 Cl 1.98 Fe 3.13 Na 2.57<br>C 41 78 H 4.28 N 11.11 Gd 17.58 Cl 2.05 Fe 3.18 Na 2.64 |
| $Mn^{3+}$ | HOAc | 6 | 120 | 83 | C 41.69 H 4.18 N 10.98 Gd 17.61 Cl 1.98 Mn 3.08 Na 2.57<br>C 41.60 H 4.27 N 11.10 Gd 17.55 Cl 2.07 Mn 3.00 Na 2.63 |
| $Co^{3+}$ | HOAc | 6 | 120 | 86 | C 41.59 H 4.17 N 10.95 Gd 17.57 Cl 1.98 Co 3.29 Na 2.57<br>C 41.66 H 4.23 N 10.88 Gd 17.50 Cl 2.00 Co 3.38 Na 2.50 |
| $Lu^{3+}$ | HOAc/H$_2$O 1:1 | 5 | 100 | 84 | C 39.07 H 3.91 N 10.29 Gd 16.50 Cl 1.86 Lu 9.18 Na 2.41<br>C 39.15 H 3.98 N 10.40 Gd 16.62 Cl 1.97 Lu 9.29 Na 2.50 |
| $Al^{3+}$ | HOAc/CHCl$_3$ 1:1 | 8 | 80 | 90 | C 42.35 H 4.24 N 11.17 Gd 17.89 Al 1.53 Cl 2.02 Na 2.62<br>C 42.28 H 4.32 N 11.20 Gd 17.99 Al 1.60 Cl 1.96 Na 2.69 |
| $Cr^{3+}$ | HOAc/CHCl$_3$ 1:1 | 8 | 70 | 89 | C 41.76 H 4.18 N 11.00 Gd 17.64 Cl 1.99 Cr 2.92 Na 2.58<br>C 41.87 H 4.25 N 11.17 Gd 17.77 Cl 2.08 Cr 2.81 Na 2.67 |
| $Ni^{2+}$ | DMSO/H$_2$O/HOAc 1:1:1 | 4 | 90 | 88 | C 42.44 H 4.25 N 11.18 Gd 17.93 Na 2.62 Ni 3.35<br>C 42.41 H 4.30 N 11.28 Gd 18.00 Na 2.71 Ni 3.49 |
| $Cu^{2+}$ | HOAc | 4 | 120 | 88 | C 42.32 H 4.24 N 11.15 Gd 17.88 Cu 3.61 Na 2.61<br>C 42.25 H 4.32 N 11.07 Gd 18.00 Cu 3.70 Na 2.69 |
| $Mg^{2+}$ | HCO$_2$H/CHCl$_3$ 1:1 | 5 | 70 | 87 | C 43.20 H 4.34 N 11.40 Gd 18.28 Mg 1.41 Na 2.67<br>C 43.31 H 4.40 N 11.26 Gd 18.40 Mg 1.47 Na 2.73 |
| $Zn^{2+}$ | HOAc/DMF 1:1 | 5 | 100 | 81 | C 42.28 H 4.24 N 11.13 Gd 17.86 Na 2.61 Zn 3.71<br>C 42.36 H 4.36 N 11.24 Gd 17.72 Na 2.77 Zn 3.82 |

TABLE 2-continued

Incorporation of Metal Ions in the Gadolinium Complex of Porphyrins from Instructions 2

| Metall | Lösungsmittel | Zeit [h] | Temperatur [° C.] | Ausbeute [%] | Elementaranalyse [berechnet/gefunden] |
|---|---|---|---|---|---|
| Sn$^{2+}$ | HOAc/CHCl$_3$ 1:1 | 8 | 70 | 83 | C 41.04 H 4.11 N 10.81 Gd 17.63 Na 2.53 Sn 6.54 C 41.20 H 4.18 N 10.91 Gd 17.56 Na 2.59 Sn 6.45 |
| VO$^{2+}$ | HOAc/CHCl$_3$ 1:1 | 8 | 70 | 85 | C 42.25 H 4.23 N 11.12 Gd 17.84 Na 2.61 V 2.89 C 42.30 H 4.24 N 11.21 Gd 17.77 Na 2.98 V 2.99 |

[Key to Table 2:]
Metall = Metal
Lösungsmittel = Solvent
Ziet [h] = Time [hours]
Temperatur [° C.] = Temperature [° C.]
Ausbeute [%] = Yield [%]
Elementaranalyse [berechnet/gefunden] = Elementary Analysis [theoretical/empirical]

TABLE 3

Incorporation of Metal Ions in the Gadolinium Complex of Porphyrins from Instructions 3

| Metall | Lösungsmittel | Zeit [h] | Temperatur [° C.] | Ausbeute [%] | Elementaranalyse [berechnet/gefunden] |
|---|---|---|---|---|---|
| Fe$^{3+}$ | HOAc/H$_2$O 1:1 | 5 | 90 | 89 | C 45.34 H 5.07 N 13.22 Cl 1.86 Fe 2.93 Gd 16.49 C 45.39 H 5.17 N 13.30 Cl 1.98 Fe 3.00 Gd 16.62 |
| Mn$^{3+}$ | HOAc/DMF 1:1 | 6 | 100 | 84 | C 45.36 H 5.08 N 13.22 Cl 1.86 Gd 16.50 Mn 2.88 C 45.51 H 5.15 N 13.07 Cl 1.98 Gd 16.65 Mn 2.76 |
| Co$^{3+}$ | HOAc/CHCl$_3$ 1:1 | 8 | 70 | 85 | C 45.26 H 5.06 N 13.20 Cl 1.86 Co 3.08 Gd 16.46 C 45.44 H 5.01 N 13.32 Cl 1.73 Co 3.17 Gd 16.59 |
| Lu$^{3+}$ | HOAc | 8 | 90 | 86 | C 42.67 H 4.77 N 12.44 Cl 1.75 Gd 15.52 Lu 8.63 C 42.87 H 4.80 N 12.58 Cl 1.87 Gd 15.65 Lu 8.78 |
| Al$^{3+}$ | HOAc | 8 | 90 | 87 | C 46.03 H 5.15 N 13.42 Cl 1.89 Al 1.44 Gd 16.74 C 43.16 H 5.02 N 14.57 Cl 2.00 Al 1.51 Gd 16.88 |
| Cr$^{3+}$ | HCO$_2$H/CHCl$_3$ 1:1 | 6 | 70 | 91 | C 45.43 H 5.08 N 13.24 Cl 1.86 Cr 2.73 Gd 16.52 C 45.54 H 4.97 N 13.10 Cl 1.99 Cr 2.87 Gd 16.66 |
| Ni$^{2+}$ | HOAc/CHCl$_3$ 1:1 | 6 | 70 | 89 | C 46.13 H 5.16 N 13.45 Gd 16.77 Ni 3.13 C 46.20 H 5.22 N 13.57 Gd 16.90 Ni 3.21 |
| Cu$^{2+}$ | HOAc/DMSO/H$_2$O 1:1:1 | 5 | 90 | 92 | C 46.01 H 5.15 N 13.41 Cu 3.38 Gd 16.73 C 46.19 H 5.22 N 13.52 Cu 3.50 Gd 16.58 |
| Mg$^{2+}$ | HOAc | 5 | 100 | 88 | C 46.99 H 5.26 N 13.70 Gd 17.09 Mg 1.32 C 46.89 H 5.40 N 13.85 Gd 17.28 Mg 1.38 |
| Zn$^{2+}$ | HOAc/CHCl$_3$ 1:1 | 6 | 70 | 84 | C 45.96 H 5.14 N 13.40 Gd 16.71 Zn 3.48 C 46.15 H 5.21 N 13.27 Gd 16.82 Zn 3.59 |
| Sn$^{2+}$ | HOAc | 6 | 100 | 85 | C 44.70 H 5.00 N 13.03 Gd 16.25 Sn 6.14 C 44.81 H 5.11 N 12.88 Gd 16.40 Sn 6.21 |
| VO$^{2+}$ | HOAc | 8 | 100 | 86 | C 45.92 H 5.14 N 13.39 Gd 16.70 V 2.71 C 46.08 H 5.19 N 13.51 Gd 16.58 V 2.81 |

[Key to Table 3:]
Metall = Metal
Lösungsmittel = Solvent
Ziet [h] = Time [hours]
Temperatur [° C.] = Temperature [° C.]
Ausbeute [%] = Yield [%]
Elementaranalyse [berechnet/gefunden] = Elementary Analysis [theoretical/empirical]

TABLE 4

Incorporation of Metal Ions in the Gadolinium Complex of Prophyrins from Instructions 4

| Metall | Lösungsmittel | Zeit [h] | Temperatur [° C.] | Ausbeute [%] | Elementaranalyse [berechnet/gefunden] |
|---|---|---|---|---|---|
| Fe$^{3+}$ | HCO$_2$H | 7 | 100 | 92 | C 44.95 H 5.09 N 12.19 Cl 1.54 Fe 2.43 Gd 13.69 Na 2.00 S 2.79 C 45.16 H 5.20 N 12.28 Cl 1.61 Fe 2.52 Gd 13.57 Na 2.15 S 2.92 |
| Mn$^{3+}$ | HOAc | 6 | 120 | 87 | C 44.97 H 5.09 N 12.20 Cl 1.54 Gd 13.69 Mn 2.39 Na 2.00 S 2.79 C 45.13 H 5.01 N 12.38 Cl 1.48 Gd 13.78 Mn 2.46 Na 2.12 S 2.90 |
| Co$^{3+}$ | HOAc/DMF 1:1 | 5 | 120 | 85 | C 44.89 H 5.08 N 12.17 Cl 1.54 Co 2.56 Gd 13.67 Na 2.00 S 2.79 C 45.00 H 4.96 N 12.04 Cl 1.62 Co 2.66 Gd 13.54 Na 2.08 S 2.68 |
| Lu$^{3+}$ | HOAc/DMF 1:1 | 6 | 100 | 86 | C 42.74 H 4.84 N 11.59 Cl 1.47 Gd 13.01 Lu 7.24 Na 1.90 S 2.65 C 42.89 H 4.93 N 11.73 Cl 1.58 Gd 13.21 Lu 7.32 Na 2.03 S 2.77 |

TABLE 4-continued

Incorporation of Metal Ions in the Gadolinium Complex of Prophyrins from Instructions 4

| Metall | Lösungsmittel | Zeit [h] | Temperatur [° C.] | Ausbeute [%] | Elementaranalyse [berechnet/gefunden] |
|---|---|---|---|---|---|
| Al$^{3+}$ | HOAc | 7 | 100 | 88 | C 45.52 H 5.15 N 12.35 Cl 1.56 Al 1.19 Gd 13.86 Na 2.03 S 2.83 |
| | | | | | C 45.45 H 5.22 N 12.50 Cl 1.63 Al 1.16 Gd 13.74 Na 2.00 S 2.95 |
| Cr$^{2+}$ | HCO$_2$H | 6 | 100 | 87 | C 45.03 H 5.10 N 12.21 Cl 1.55 Cr 2.27 Gd 13.71 Na 2.00 S 2.80 |
| | | | | | C 44.91 H 5.15 N 12.30 Cl 1.61 Cr 2.39 Gd 13.88 Na 2.11 S 2.92 |
| Ni$^{2+}$ | HOAc/DMF 1:1 | 4 | 80 | 89 | C 45.60 H 5.16 N 12.37 Gd 13.88 Na 2.03 Ni 2.59 S 2.83 |
| | | | | | C 45.79 H 5.11 N 12.50 Gd 13.97 Na 2.10 Ni 2.67 S 2.90 |
| Cu$^{2+}$ | HOAc/DMF 1:1 | 6 | 110 | 92 | C 45.50 H 5.15 N 12.34 Cu 2.80 Gd 13.85 Na 2.03 S 2.83 |
| | | | | | C 45.65 H 5.00 N 12.49 Cu 2.90 Gd 13.74 Na 2.10 S 2.91 |
| Mg$^{2+}$ | HCO$_2$H | 5 | 100 | 85 | C 46.30 H 5.24 N 12.56 Gd 14.10 Mg 1.09 Na 2.06 S 2.87 |
| | | | | | C 46.44 H 5.12 N 12.69 Gd 14.25 Mg 1.13 Na 2.00 S 3.05 |
| Zn$^{2+}$ | HOAc/DMF 1:1 | 5 | 100 | 84 | C 45.46 H 5.15 N 12.33 Gd 13.84 Na 2.02 S 2.82 Zn 2.88 |
| | | | | | C 45.57 H 5.22 N 13.50 Gd 14.00 Na 2.08 S 2.88 Zn 2.97 |
| Sn$^{2+}$ | HOAc | 6 | 100 | 84 | C 44.42 H 5.03 N 12.05 Gd 13.53 Na 1.98 S 2.76 Sn 5.11 |
| | | | | | C 44.51 H 5.12 N 12.17 Gd 13.69 Na 2.02 S 2.84 Sn 5.21 |
| VO$^{2+}$ | HOAc | 6 | 100 | 86 | C 45.43 H 5.14 N 12.32 Gd 13.83 Na 2.02 S 2,82 V 2.24 |
| | | | | | C 45.52 H 5.20 N 13.18 Gd 13.92 Na 2.10 S 2.71 V 2.31 |

[Key to Table 4:]
Metall = Metal
Lösungsmittel = Solvent
Ziet [h] = Time [hours]
Temperatur [° C.] = Temperature [° C.]
Ausbeute [%] = Yield [%]
Elementaranalyse [berechnet/gefunden] = Elementary Analysis [theoretical/empirical]

What is claimed is:

1. A process for the production of a metalloporphyrin-metal complex conjugate, said process comprising: converting a porphyrin-metal complex conjugate into a metallporphyrin-metal complex conjugate by reaction with a metal acetylacetonate in a solvent or solvent mixture selected from water, formic acid, acetic acid. dimethylformamide. dimethyl sulfoxide, chloroform or a mixture of at least two of these solvents, at a temperature from room temperature to 150° C. in concentrations of 3–30% in a metalloporphyrin-metal complex conjugate.

2. A process according to claim 1, wherein said metallorporphyrin-metal complex conjugate is of formula I

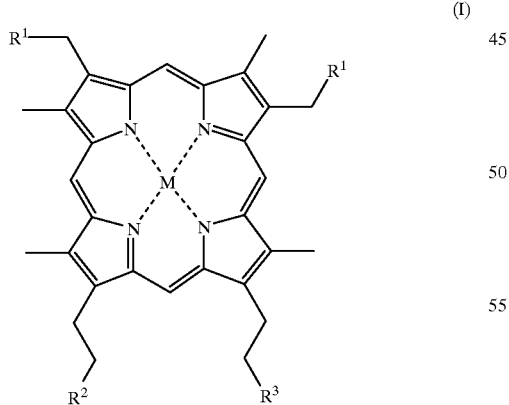

(I)

wherein
M stands for a metal ion of magnesium, aluminum, chromium, manganese, iron, cobalt, nickel, copper, zinc, gallium, technetium, indium, tin, europium, lutetium, thallium, bismuth or oxovanadium (IV),
R$^1$ stands for a hydrogen atom, a straight-chain C$_1$–C$_6$ alkyl radical, a C$_7$–C$_{12}$ aralkyl radical or OR', R' is a hydrogen atom or a C$_1$–C$_3$ alkyl radical,
R$^2$ is —CO—Z, —(NH)$_o$—(A)$_q$—NH—D, or a group according to the definition of R$^3$,
Z is —OL,
L is an inorganic or organic cation or a C$_1$–C$_4$ alkyl radical,
A means a phenylenoxy group or a C$_1$–C$_{12}$ alkylene or C$_7$–C$_{12}$ aralkylene group that is interrupted by one or more oxygen atoms,
o and q, independently or one another, mean the numbers 0 or 1,
D means a hydrogen atom or a group —CO—A—(COOL)$_o$—(H)$_m$, with m equal to 0 or 1 and provided that the sum of m and o is equal to 1,
R$^3$ stands for a group —(C=Q)(NR$^4$)$_o$—(A)$_q$—(NR$^5$)—K,
Q stands for an oxygen atom or for two hydrogen atoms,
R$^4$ means an —(A)$_q$—H group, and
K means a complexing agent of general formula (IIa), (IIb), (IIc), (IId) or (IIe),
R$^5$ is —(A)$_q$—H if K is a complexing agent of Formula (Ia), and
is a hydrogen atom or —CO—A—(COOL)$_o$—(H)$_m$, with m equal to 0 or 1 and provided that the sum of m and o is equal to 1, if K is a complexing agent of Formula (IIb), (IIc), (IId) or (IIe),
provided that a direct oxygen-nitrogen bond is not allowed

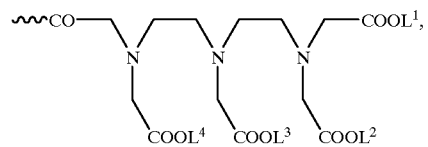

(IIa)

-continued

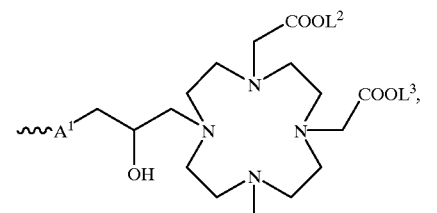
(IIb)

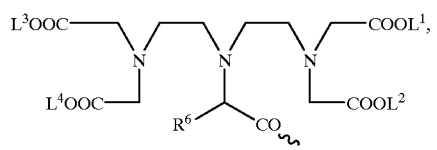
(IIc)

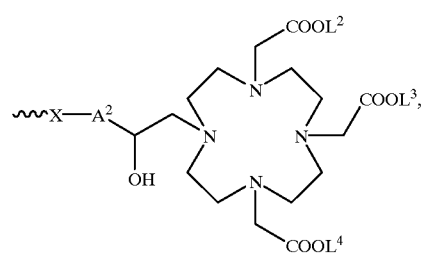
(IId)

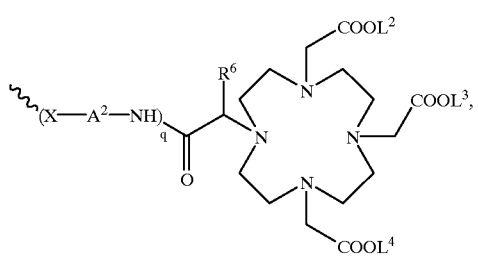
(IIe)

A$^1$ is phenylenoxy or a C$_1$–C$_{12}$ alkylene or C$_7$–C$_{12}$ aralkylene that is interrupted by one or more oxygen atoms, R$^6$ stands for a hydrogen atom, a straight-chain or branched C$_1$–C$_7$ alkyl group, a phenyl or benzyl group, A$^2$ stands for a phenylene group, a —CH$_2$—NHCO—CH$_2$—CH(CH$_2$COOH)—C$_6$H$_4$-β-group, a phenylenoxy group or a C$_1$–C$_{12}$ alkylene or C$_7$–C$_{12}$ alkylene group that is optionally interrupted by one or more oxygen atoms, 1 to 3 —NHCO and/or 1–3 CONH groups and/or substituted with by 1 to 3—(CH$_2$)$_{0-5}$COOH groups, β stands for the binding site to X, X stands for a —CO— or NHCS group, and L$^1$, L$^2$, L$^3$ and L$^4$, independently of one another, stand for a metal ion equivalent of an element of atomic numbers 20–32, 37–39, 42–51 or 57–83, provided that at least two of these substituents stand for a metal ion equivalent, and other anions are present to compensate for optionally present charges in the metalloporphyrinmetal complex conjugate and in which free carboxylic acid groups that are not required for complexing can also be present as salts with physiologically compatible inorganic and/or organic cations, or as esters or as amides; and said porphyrin-metal complex conjugate is of formula (III)

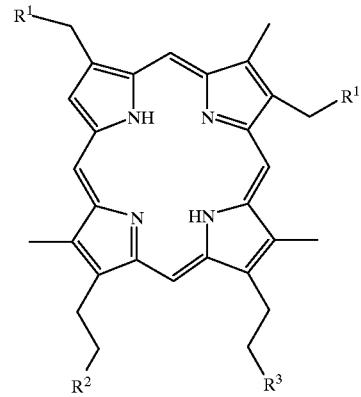
(III)

wherein said metal acetylacetonate is of metal M.

3. A process according to claim 2, wherein metal M stands for manganese, iron, copper or zinc.

4. A process according to claim 2, wherein temperatures of 50°–130° C. are maintained.

5. A process according to claim 2, wherein said metalloporphyrin-metal complex conjugate is:

{μ-[{16,16'-[zinc(II)-7,12-diethyl-3,8,13,17-tetramethylporphyrin-2,18-diyl]-bis[3,6,9,-tris(carboxylmethyl)-11,14-dioxo-3,6,9,12,13-pentaazahexadecanoato]}(8-)]}-digadolinato(2-), disodium;

{μ-[{16,16'-[Acetatomanganese(III)-7,12-diethyl-3,8,13,17-tetramethylporphyrin-2,18-diyl]-bis[3,6,9-tris(carboxymethyl)-11,14-dioxo-3,6,9,12,13-pentaazahexadecanoato]}-(8-)]}digadolinato(2-), disodium;

{μ-[{16,16'-[Acetatoiron(III)-7,12-diethyl-3,8,13,17-tetramethylporphyrin-2,18-diyl]-bis[3,6,9-tris(carboxymethyl)-11,14-dioxo-3,6,9,12,13-pentaazahexadecanoato]}(8-)]}digadolinato(2-), disodium; or {μ-[{16,16'-[Copper(II)-7,12-diethyl-3,8,13,17-tetramethylporphyrin-2,18-diyl]-bis[3,6,9-tris(carboxymethyl)-11,14-dioxo-3,6,9,12,13-pentaazahexadecanoato]}(8-)]}digadolinato(2-), disodium.

6. A process according to claim 1, wherein said porphyrin-metal complex conjugate is a complex of at least one ion of an element of atomic numbers 20–32, 37–39, 42–51, or 57–83.

7. A process according to claim 1, wherein the metalloporphyrin portion of said metalloporphyrin-metal complex conjugate contains a metal ion of magnesium, aluminum, chromium, manganese, iron, cobalt, nickel, copper, zinc, gallium, technetium, indium, tin, europium, lutetium, thallium, bismuth or oxovanadium (IV).

8. A process according to claim 6, wherein the metalloporphyrin portion of said metalloporphyrin-metal complex conjugate contains a metal ion of magnesium, aluminum, chromium, manganese, iron, cobalt, nickel, copper, zinc, gallium, technetium, indium, tin, europium, lutetium, thallium, bismuth or oxovanadium (IV).

9. A process according to claim 2, wherein R$^1$ is a straight-chain C$_1$–C$_3$ alkyl.

10. A process according to claim 2, wherein R' is methyl, ethyl, propyl or isopropyl.

11. A process according to claim 2, wherein R$^1$ is benzyl or 4-methoxybenzyl.

12. A process according to claim 2, wherein L is a lithium ion, a potassium ion, or a sodium ion.

13. A process according to claim 2, wherein L is the cation of ethanolamine, diethanolamine, morpholine, glucamine, N,N-dimethylglucamine or meglumine.

14. A process according to claim 2, wherein Z is methyl or ethyl.

15. A process according to claim 2, wherein $R^2$ and $R^3$ are the same.

16. A process according to claim 2, wherein $R^2$ and $R^3$ are each, independently, —CONHNH—K, —CONH—$(CH_2)_2$—NH—K, —CONH—$(CH_2)_3$—NH—K, —CONH—$(CH_2)_4$—NH—K or —CONH—$(CH_2)_2$—O—$(CH_2)_2$—NH—K.

17. A process according to claim 2, wherein $R^2$ and $R^3$ are both —CONHNH—K, —CONH—$(CH_2)_2$—NH—K, —CONH—$(CH)_2)_3$—NH—K, —CONH—$(CH_2)_4$—NH—K or —CONH—$(CH_2)_2$—O—$(CH_2)_2$—NH—K.

18. A process according to claim 2, wherein $R^2$ and $R^3$ are each —CONHNH—K.

19. A process according to claim 2, wherein Q is oxygen.

20. A process according to claim 2, wherein $R^4$ is hydrogen.

21. A process according to claim 2, wherein K is a complexing agent of formula IIa or IIe.

22. A process according to claim 2, wherein $R^6$ is H or methyl.

23. A process according to claim 2, wherein $A^2$ is —$CH_2$—, —$(CH_2)_2$—, —$CH_2OC_6H_5$—β, —$CH_2$—$OCH_2$—, —$C_6H_5$—, or —$CH_2$—NHCO—$CH_2$—CH($CH_2COOH$)—$C_6H_5$β, wherein β stands for the binding site to X.

24. A process according to claim 2, wherein X is CO.

25. A process according to claim 1, wherein conversion of the porphyrin-metal complex conjugate into a metalloporphyrin-metal complex conjugate is conducted at a temperature of 70–120° C.

26. A process according to claim 2, wherein conversion of the porphyrin-metal complex conjugate into a metalloporphyrin-metal complex conjugate is conducted at a temperature of 70–120° C.

27. A process according to claim 1, wherein said solvent or solvent mixture contains acetic acid.

28. A process according to claim 2, wherein said solvent or solvent mixture contains acetic acid.

* * * * *

UNITED STATES PATENT AND TRADEMARK OFFICE
CERTIFICATE OF CORRECTION

PATENT NO. : 6,194,566 B1  
DATED : February 27, 2001  
INVENTOR(S) : Platzek et al.

Page 1 of 1

It is certified that error appears in the above-identified patent and that said Letters Patent is hereby corrected as shown below:

Column 14, claim 2,  
Line 52, reads "(Ia)" should read -- (IIa) --;

Column 18, claim 23,  
Line 4, reads "$C_6H_5\beta$" should read -- $C_6H_5\text{-}\beta$ --

Signed and Sealed this

Ninth Day of April, 2002

Attest:

Attesting Officer

JAMES E. ROGAN  
*Director of the United States Patent and Trademark Office*